(12) United States Patent
Andersson

(10) Patent No.: US 6,792,941 B2
(45) Date of Patent: Sep. 21, 2004

(54) INHALATION DEVICE

(75) Inventor: Malin Andersson, Stockholm (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/316,123

(22) Filed: Dec. 11, 2002

(65) Prior Publication Data

US 2003/0084899 A1 May 8, 2003

Related U.S. Application Data

(63) Continuation of application No. 09/331,870, filed as application No. PCT/SE99/00503 on Mar. 26, 1999, now abandoned.

(30) Foreign Application Priority Data

Mar. 27, 1998 (SE) .............................................. 9801077

(51) Int. Cl.[7] .............................................. A61M 11/00
(52) U.S. Cl. ............................ 128/200.23; 128/200.14; 128/203.23
(58) Field of Search ................... 128/200.14, 200.23, 128/203.15, 200.22, 203.12, 203.19, 203.33

(56) References Cited

U.S. PATENT DOCUMENTS

| | | | |
|---|---|---|---|
| 4,678,106 A | | 7/1987 | Newell et al. |
| 5,408,994 A | * | 4/1995 | Wass et al. ............. 128/203.15 |
| 5,447,150 A | | 9/1995 | Bacon |
| 5,692,492 A | * | 12/1997 | Bruna et al. ............ 128/200.23 |
| 6,415,784 B1 | * | 7/2002 | Christrup et al. ....... 128/200.23 |
| 6,510,847 B1 | * | 1/2003 | Helgesson et al. ...... 128/200.23 |
| 6,595,205 B2 | * | 7/2003 | Andersson et al. ..... 128/200.23 |

FOREIGN PATENT DOCUMENTS

EP   0 448 204 A1   9/1991

* cited by examiner

Primary Examiner—Glenn K. Dawson
Assistant Examiner—Darwin P Erezo
(74) Attorney, Agent, or Firm—Nixon & Vanderhye

(57) ABSTRACT

An actuator for an inhaler for delivering medicament by inhalation, comprising: a housing (14) for receiving a canister (8) comprising a body (10) which defines a chamber containing medicament and a valve stem (12) which extends from the body (10); a nozzle block (18) for receiving the valve stem (12) of the canister (8); a mouthpiece for providing medicament from the nozzle block (18) to the mouth of a user; and at least one actuating member (54, 56) for manual engagement by a user in applying a force to actuate the canister (8), wherein the at least one actuating member (54, 56) is disposed such that the actuating force is applied substantially laterally relative to the longitudinal axis of the canister (8) and configured when being acted upon to cause relative movement of the body (10) and the valve stem (12) of the canister (8).

13 Claims, 3 Drawing Sheets

INHALATION DEVICE

This application is a continuation of application Ser. No. 09/331,870, filed Jun. 29, 1999 now abandoned, which is a 371 of PCT/SE99/00503 filed Mar. 26, 1999, the entire content of which is hereby incorporated by reference in this application.

The present invention relates to an actuator for an inhaler for administering medicament by inhalation and to an inhaler including the same.

BACKGROUND OF THE INVENTION

EP-A0448204 discloses one such actuator for delivering metered doses of medicament from an aerosol canister which comprises a body which defines a chamber containing medicament in a propellant under pressure, a valve stem which extends axially from one end of the body and an internal metering valve which is normally biased to a closed position and opened to deliver a metered dose of medicament when the valve stem is depressed. This actuator comprises an elongate tubular member which is configured to receive the canister such that the bottom wall of the body of the canister extends therefrom so as to be depressable by a user, a mouthpiece for guiding medicament to the mouth of a user and a nozzle block for receiving the valve stem of the canister and delivering medicament from the canister into the mouthpiece.

Such actuators have been used successfully for some time, but do, however, require a user to be able to develop sufficient force to open the metering valve of the canister, which force corresponds principally to the spring force of the closure spring in the metering valve. Traditionally, the metering valves of aerosol canisters containing chlorofluorocarbon based formulations have required a closure spring with a spring force of about 20 N. However, the metering valves of aerosol canisters containing the more recent alternative propellants, such as hydrofluorocarbons, require closure springs with a much higher spring force, typically about 40 N.

As will be appreciated, the development of such forces is often difficult, particularly for paediatric and geriatric patients, where the distance between the force application points is considerable, in being necessarily greater than the height of the canister. In a standard actuator the distance between the force application points is at least 60 mm.

SUMMARY OF THE INVENTION

It is therefore an aim of the present invention to provide an actuator for an inhaler for delivering medicament by inhalation which is configured such that the actuating force can be applied by a user in a more ergonomically favourable manner.

Accordingly, the present invention provides an actuator for an inhaler for delivering medicament by inhalation, comprising: a housing for receiving a canister comprising a body which defines a chamber containing medicament and a valve stem which extends from the body; a nozzle block for receiving the valve stem of the canister; a mouthpiece for providing medicament from the nozzle block to the mouth of a user, and at least one actuating member for manual engagement by a user in applying a force to actuate the canister, wherein the at least one actuating member is disposed such that the actuating force is applied substantially laterally relative to the longitudinal axis of the canister and configured when being acted upon to cause relative movement of the body and the valve stem of the canister.

With this configuration, the distance between the force application points is considerably less than in a standard actuator; the diameter of a standard actuator being substantially less than the height. Indeed, the distance between the force application points can be reduced typically to about 30 mm. This configuration is particularly advantageous as, where the actuating force is applied between a finger, typically the index finger, and the thumb, the closer the spacing between the finger and the thumb the more easily the required force can be generated.

In a preferred embodiment the at least one actuating member is configured when being acted upon to move the body of the canister in relation to the valve stem of the canister.

Preferably, the at least one actuating member includes an outwardly-facing surface for manual engagement by a user and an- inwardly-facing surface which in use bears against a surface of the canister.

In a preferred embodiment the bearing surface of the canister is a junction between a bottom wall and a side wall of the body of the canister.

Preferably, the inwardly-facing surface of the at least one actuating member includes an inclined surface portion over which the bearing surface of the canister in use progressively slides.

In one embodiment the inclined surface portion of the inwardly-facing surface is a substantially planar surface.

Preferably, the inclined surface portion of the inwardly-facing surface encloses an acute angle of more than 45 degrees with the longitudinal axis of the canister.

More preferably, the inclined surface portion of the inwardly-facing surface encloses an acute angle of at least 60 degrees with the longitudinal axis of the canister.

With this configuration, the inclined surface portion of the inwardly-facing surface of the at least one actuating member acts by the inclined plane effect to apply an amplified force to the body of the canister relative to the force applied by the user to the at least one actuating member, thereby allowing a user to apply a lower force, albeit over a greater distance, to actuate the canister than would be required if the force were applied axially directly to the bottom wall of the body of the canister.

In another embodiment the inclined surface portion of the inwardly-facing surface of the at least one actuating member is a curved surface.

Preferably, the tangent of the inclined surface portion of the inwardly-facing surface encloses an acute angle of more than 45 degrees with the longitudinal axis of the canister.

More preferably, the tangent of the inclined surface portion of the inwardly-facing surface encloses an acute angle of at least 60 degrees with the longitudinal axis of the canister.

As mentioned above, this configuration acts by the inclined plane effect to apply an amplified force to the body of the canister relative to the force applied by the user to the at least one actuating member.

In a preferred embodiment the at least one actuating member is hinged.

Preferably, the outwardly-facing surface of the at least one actuating member extends a greater distance from the hinge than the inwardly-facing surface of the at least one actuating member.

With this configuration, the at least one actuating member acts by the lever effect to apply an amplified force to the body of the canister relative to the force applied by the user to the at least one actuating member, thereby, similarly to the inclined plane effect described hereinabove, allowing a user to apply a lower force to actuate the canister than would be required if the force were applied axially directly to the bottom wall of the body of the canister. It will be appreciated that a significant mechanical advantage would be achieved where the at least one actuating member is configured to embody both this lever effect and the above-described inclined plane effect.

Preferably, the actuator further comprises a cover member which comprises a body part which is movably mounted to the housing between a first position in which the mouthpiece is disposed therewithin and a second position in which the mouthpiece is exposed.

Preferably, the body part is rotatably mounted to the housing.

Preferably, the body part includes an opening through which the mouthpiece extends in the second position of the body part and the cover member further comprises a flap which is movably mounted to the body part between a first position in which the opening in the body part is closed and a second position in which the opening in the body part is open.

Preferably, the at least one actuating member is integral with the body part.

In a preferred embodiment the actuator comprises first and second actuating members.

Preferably, the actuating members are oppositely directed.

The present invention further provides an actuator for an inhaler for delivering medicament by inhalation, comprising: a housing for receiving a canister comprising a body which defines a chamber containing medicament and a valve stem which extends from the body; a nozzle block for receiving the valve stem of the canister; a mouthpiece for providing medicament from the nozzle block to the mouth of a user, and first and second actuating members for manual engagement by a user in applying a force to actuate the canister, wherein the actuating members are opposed and movably mounted relative to the housing.

The present invention also extends to inhalers comprising the above-described actuators and a canister containing medicament.

BRIEF DESCRIPTION OF THE DRAWINGS

A preferred embodiment of the present invention will now be described by way of example only with reference to the accompanying drawings, in which.

DETAILED DESCRIPTION OF THE PREFERRED EMBODIMENTS

Figure 1:
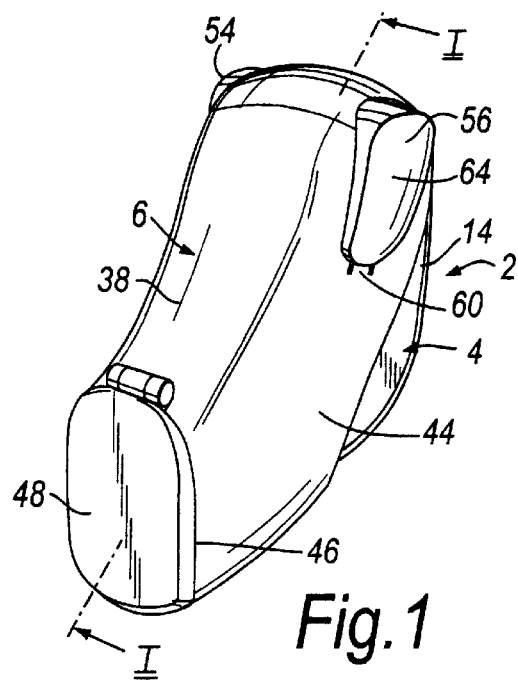
FIG. 1 illustrates a perspective view of an inhaler in accordance with a preferred embodiment of the present invention in the closed or inoperable configuration.
Figure 2:
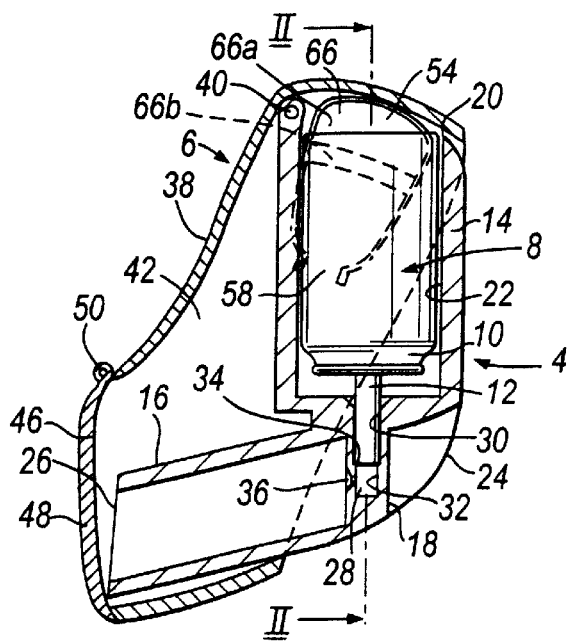
FIG. 2 illustrates a vertical sectional view along section I—I in FIG. 1.
Figure 3:
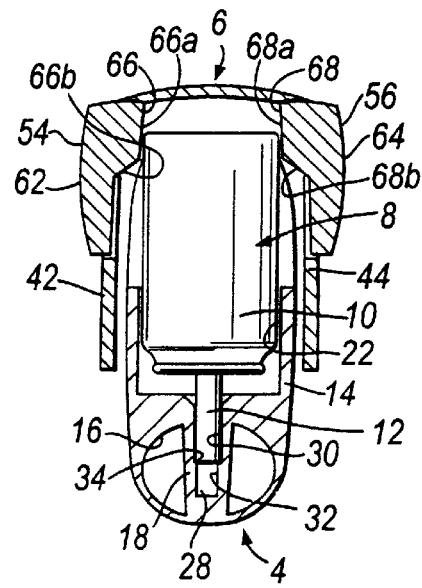
FIG. 3 illustrates a vertical sectional view along section II—II in FIG. 2.

The inhaler comprises an actuator 2 which comprises a main body 4 and a hinged cover member 6 and an aerosol canister 8 which contains medicament and is fitted in the actuator 2. The aerosol canister 8 comprises a body 10 which defines a chamber containing medicament in a propellant under pressure, a valve stem 12 which extends axially from one end of the body 10 and an internal metering valve (not illustrated) which is normally biased to a closed position and opened to deliver a metered dose of medicament from the canister 8 when the valve stem 12 is depressed.

The main body 4 comprises a housing 14 in which the canister 8 is in use fitted, a tubular section 16, a major part of which defines the mouthpiece which is in use gripped in the lips of a user, and a nozzle block 18 for receiving the valve stem 12 of the canister 8. In this embodiment the main body 4 is formed as a single integral unit, preferably of a plastics material.

The housing 14 includes an opening 20 at one, the upper, end thereof through which the canister 8 is in use fitted and defines a cavity 22, in this embodiment substantially circular in section, which houses the canister 8.

The tubular section 16, which in part defines the mouthpiece, extends substantially transversely beneath the other, lower, end of the housing 14 and includes a first, inlet opening 24 at one, the rear, end thereof through which air is in use inhaled and a second, outlet opening 26 at the other, forward, end thereof through which air drawn through the inlet opening 24 and propellant containing medicament delivered from the canister 8 is in use inhaled.

The nozzle block 18 includes a tubular bore 28 for receiving the valve stem 12 of the canister 8 which is co-axial with the longitudinal axis of the housing 14. The tubular bore 28 is open at one, the upper, end thereof and includes an upper part 30 having an internal dimension substantially the same as the outer dimension of the valve stem 12 and a lower part 32 having a smaller internal dimension, which parts 30, 32 together define an annular seat 34 for the distal end of the valve stem 12. The tubular bore 28 further includes a laterally-directed spray orifice 36 in the lower part 32 thereof which is configured to direct a spray into and through the tubular section 16 defining the mouthpiece.

Figure 4:
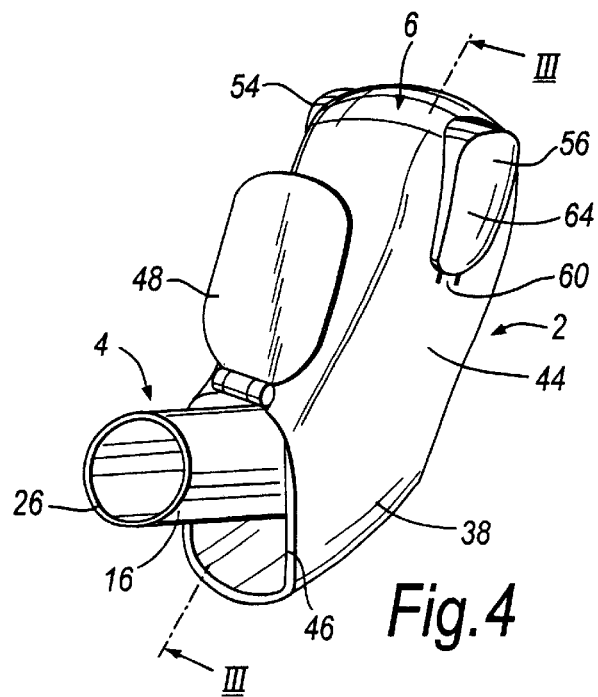
FIG. 4 illustrates a perspective view of the inhaler of FIG. I in the open or operable configuration.
Figure 5:
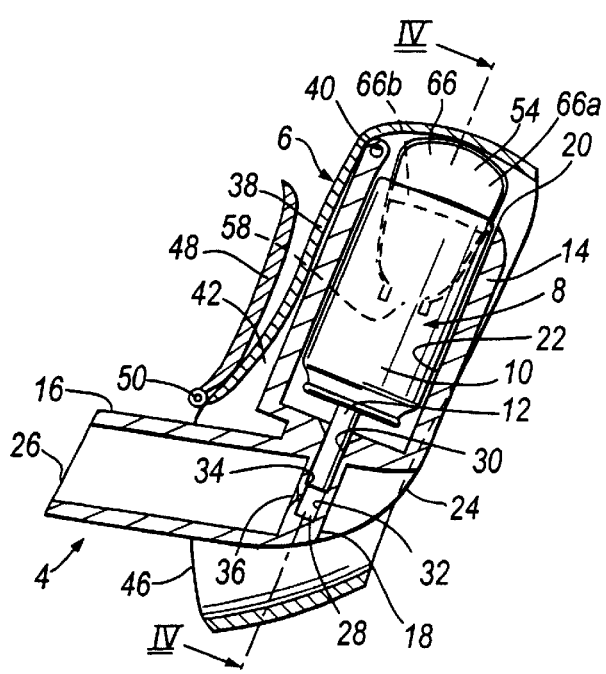
FIG. 5 illustrates a vertical sectional view along section III—III in FIG. 4, with the canister illustrated in the non-actuated position.
Figure 6:
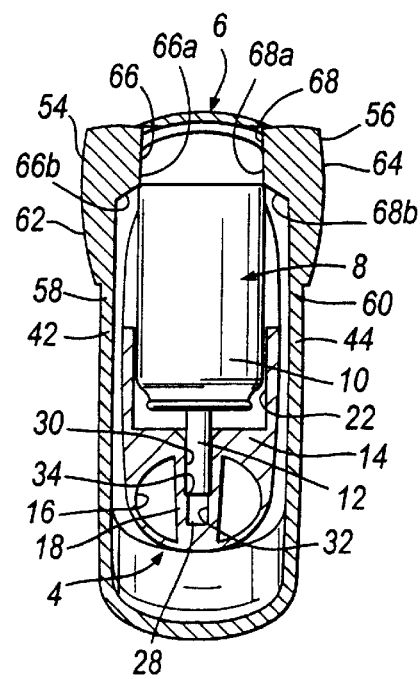
FIG. 6 illustrates a vertical sectional view along section IV—IV in FIG. 5, with the canister illustrated in the non-actuated position.
Figure 7:
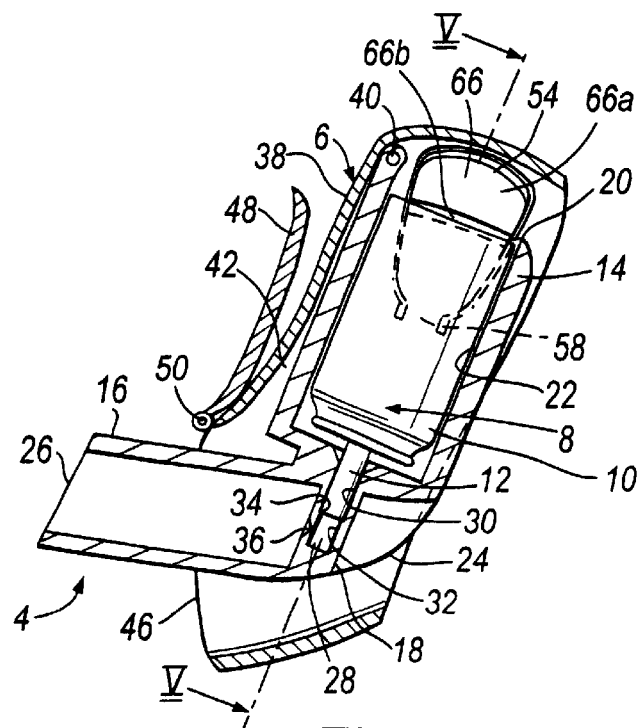
FIG. 7 illustrates a vertical sectional view along section III—III in FIG. 4, with the canister illustrated in the actuated position.
Figure 8:
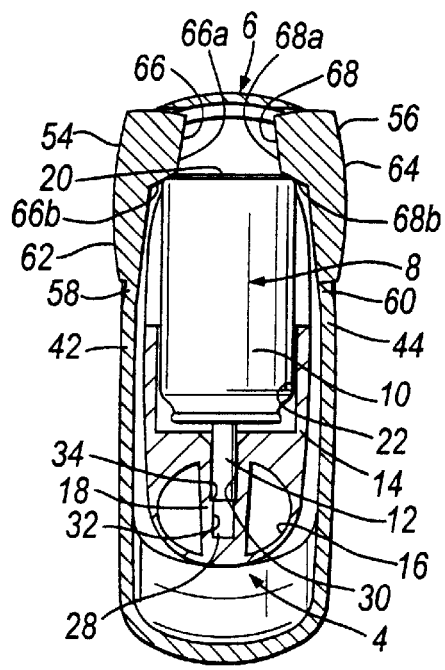
FIG. 8 illustrates a vertical sectional view along section V—V in FIG. 7, with the canister illustrated in the actuated position.

The cover member 6 comprises a body part 38 which is mounted by a hinge pin 40 to the upper end of the housing 14 of the main body 4. The body part 38 includes first and second opposed side wall members 42, 44 which encompass a part of the main body 4 and an opening 46 in a front surface thereof through which can extend the mouthpiece defined by the tubular section 16 of the main body 4. In this embodiment the body part 38 is movable between a closed or inoperable configuration (FIG. 1) in which the mouthpiece is located within the body part 38 and an open or operable configuration (FIG. 4) in which the mouthpiece extends through the opening 46 in the body part 38 such as to be able to be gripped in the lips of a user.

The cover member 6 further comprises a flap 48 which is mounted by a hinge pin 50 to the body part 38 such as to allow the opening 46 in the body part 38 to be closed and thereby enclose the mouthpiece so as to protect the same. In use, the flap 48 is raised such as to allow unimpeded access to the mouthpiece.

The cover member 6 further comprises first and second actuating members 54, 56 for providing for manual actuation of the canister 8. In a preferred embodiment, as in this embodiment, the first and second actuating members 54, 56 are connected to a respective one of the side wall members 42, 44 of the body part 38 by hinge elements 58, 60. In one embodiment, again as in this embodiment, the first and second actuating members 54, 56 are integrally formed with the body part 38, preferably in a plastics material, such that the hinge elements 58, 60 are living hinges. In another embodiment the first and second actuating members 54, 56 are components separate to the body part 38 and the hinge elements 58, 60 comprise, for example, leaf springs. In an alternative embodiment the first and second actuating members 54, 56 are not connected to the body part 38 and are slideably disposed to the body part 38.

Each actuating member 54, 56 includes an outwardly-facing surface 62, 64 which is manually acted upon by a user in the actuation of the inhaler and an inwardly-facing surface 66, 68 which is disposed adjacent the body 10 of the canister 8. Each of the opposed inwardly-facing surfaces 66, 68 includes a first, upper surface portion 66a, 68a which is substantially parallel to the longitudinal axis of the canister 8 and in the closed configuration of the inhaler is disposed adjacent the side wall of the body 10 of the canister 8 and a second, lower surface portion 66b, 68b, at least a component of which is downwardly facing and inclined with respect to the longitudinal axis of the canister 8. In this embodiment the lower surface portions 66b, 68b of the inwardly-facing surfaces 66, 68 are linear in section, but in an alternative embodiment have a curved section. As will be described in greater detail hereinbelow, the lower surface portions 66b, 68b of the inwardly-facing surfaces 66, 68 are configured as contact surfaces for acting on the junction between the bottom wall and the side wall of the body 10 of the canister 8 and depressing the body 10 of the canister 8 in the housing 14 of the main body 4 so as to deliver a metered dose of medicament from the canister 8 when the actuating members 54, 56 are pressed inwardly about the respective hinge elements 58, 60. In a preferred embodiment, where the lower surface portions 66b, 68b of the inwardly-facing surfaces 66, 68 are substantially planar, the lower surface portions 66b, 68b are configured to enclose an acute angle of more than 45 degrees with the longitudinal axis of the canister 8 such as to achieve a mechanical advantage by the inclined plane effect when acting on the junction between the bottom wall and the side wall of the body 10 of the canister 8. In the embodiment where the lower surface portions 66b, 68b of the inwardly-facing surfaces 66, 68 are curved surfaces, the curved surfaces are configured such that the tangents thereof enclose an acute angle of more than 45 degrees with the longitudinal axis of the canister 8 such as similarly to achieve a mechanical advantage by the inclined plane effect.

In use, a user takes the inhaler in the closed configuration in his or her hand. In this closed configuration the inhaler is inoperable as the upper surface portions 66a, 68a of each of the inwardly-facing surfaces 66, 68 of the actuating members 54, 56 are disposed adjacent the side wall of the body 10 of the canister 8 and pressing on the actuating members 54, 56 merely causes the upper surface portions 66a, 68a of each of the inwardly-facing surfaces 66, 68 to abut the substantially parallel surfaces of the side wall of the body 10 of the canister 8. The user then acts on the main body 4 and the cover member 6 of the inhaler, typically by squeezing together the main body 4 and the cover member 6 in a direction orthogonal to the axis of the hinge pin 40, to cause the mouthpiece defined by the tubular section 16 of the main body 4 to extend from the opening 46 in the body part 38 of the cover member 6. The user then further raises the flap 48 of the cover member 6 to the fully raised position; the flap 48 having been partially raised in acting on the main body 4 and the cover member 6 to cause the mouthpiece to extend from the opening 46. In this open configuration the inhaler is operable as the actuating members 54, 56 have been rotated relative to the canister 8 such that the junction between the bottom wall and the side wall of the body 10 of the canister 8 opposes the lower surface portions 66b, 68b of the inwardly-facing surfaces 66, 68. The user then takes the mouthpiece in his or her lips and at the same time both squeezes the actuating members 54, 56 together, typically using the thumb and the index finger, and inhales through the mouthpiece. The application of inwardly-directed opposed lateral forces to the outwardly-facing surfaces 62, 64 of the actuating members 54, 56 causes the actuating members 54, 56 to move inwardly together by rotating about the hinge elements 58, 60, which movement causes the lower surface portions 66b, 68b of the inwardly-facing surfaces 66, 68 to engage the junction between the bottom wall and the side wall of the body 10 of the canister 8 and thereby apply a downward force to the body 10 of the canister 8. In this preferred embodiment the inclined lower surface portions 66b, 68b of the inwardly-facing surfaces 66, 68 are configured so as to apply an amplified force to the body 10 of the canister 8 relative to the force applied by the user to the actuating members 54, 56. As the actuating members 54, 56 are progressively squeezed inwardly, the body 10 of the canister 8 is progressively moved downwardly relative to the valve stem 12 of the canister 8 which bears on the annular seat 34 in the tubular bore 28 in the nozzle block 18, with the junction between the bottom wall and side wall of the body 10 of the canister 8 sliding downwardly along the inclined lower surface portions 66b, 68b of the inwardly-facing surfaces 66, 68. This downward movement of the body 10 of the canister 8 continues and a point is reached where the body 10 of the canister 8 has been moved sufficiently relative to the valve stem 12 of the canister 8 as to open the metering valve of the canister 8. At this point, a metered dose of medicament is delivered from the canister 8 through the spray nozzle 36 in the nozzle block 18 and into the mouthpiece and inhaled by the user. The user then discontinues applying a force to the actuating members 54, 56 and withdraws the inhaler from his or her mouth. In no longer applying a force to the actuating members 54, 56 the body 10 of the canister 8 is driven upwardly relative to the valve stem 12 of the canister 8 under the action of the closure spring in the metering valve of the canister 8 so as to close the metering valve. The user then returns the body part 38 of the cover member 6 to the closed position in which the mouthpiece defined by the tubular section 16 of the main body 4 is disposed within the body part 38 and lowers the flap 48 so as to close the opening 46 in the body part 38.

Finally, it will be understood that the present invention is not limited to the described embodiments but can be modified in many different ways within the scope of the appended claims.

What is claimed is:

1. An actuator for an inhaler for delivering medicament by inhalation, comprising:
   a housing for receiving a canister comprising a body which defines a chamber containing medicament and a valve stem which extends from the body;
   a nozzle block for receiving the valve stem of the canister;
   a mouthpiece for providing medicament from the nozzle block to the mouth of a user; and at least one actuating member for manual engagement by a user in applying a force to actuate the canister, wherein the at least one actuating member is disposed such that the actuating force is applied substantially laterally relative to the longitudinal axis of the canister and configured when being acted upon to cause relative movement of the body and the valve stem of the canister;

said at least one actuating member including an outwardly-facing surface for manual engagement by a user and an inwardly-facing surface which in use bears against a surface of the canister, said inwardly-facing surface of said at least one actuating member including a curved inclined surface portion over which the bearing surface of the canister in use progressively slides.

2. The actuator according to claim 1, wherein the at least one actuating member is configured when being acted upon to move the body of the canister in relation to the valve stem of the canister.

3. The actuator according to claim 1, wherein the canister has a bearing surface which is a junction between a bottom wall and a side wall of the body of the canister.

4. The actuator according to claim 1, wherein the at least one actuating member is hinged.

5. The actuator according to claim 4, wherein the outwardly-facing surface of the at least one actuating member extends a greater distance from the hinge than the inwardly-facing surface of the at least one actuating member.

6. The actuator according to claim 1, further comprising a cover member which comprises a body part which is movably mounted to the housing between a first position in which the mouthpiece is disposed therewithin and a second position in which the mouthpiece is exposed.

7. The actuator according to claim 6, wherein the body part is rotatably mounted to the housing.

8. The actuator according to claim 6, wherein the body part includes an opening through which the mouthpiece extends in the second position of the body part and the cover member further comprises a flap which is movably mounted to the body part between a first position in which the opening in the body part is closed and a second position in which the opening in the body part is open.

9. The actuator according to claim 6, wherein the at least one actuating member is integral with the body part.

10. The actuator according to claim 1, comprising first and second actuating members.

11. The actuator according to claim 10, wherein the actuating members are oppositely directed.

12. An inhaler comprising the actuator of claim 1 and a canister containing medicament.

13. An actuator for an inhaler for delivering medicament by inhaling, comprising:

a housing for receiving a canister comprising a body which defines a chamber containing medicament and a valve stem which extends from the body;

a nozzle block for receiving the valve stem of the canister;

a mouthpiece for providing medicament from the nozzle block to the mouth of a user; and first and second actuating members for manual engaging by a user in applying a force to actuate the canister, wherein the actuating members are opposed and movably mounted relative to the housing;

said actuating members each including an outwardly-facing surface for manual engagement by a user and an inwardly-facing surface which in use bears against a surface of the canister, said inwardly-facing surface of each of said actuating members including a curved inclined surface portion over which the bearing surface of the canister in use progressively slides.

* * * * *